United States Patent [19]

Watson

[11] Patent Number: 4,834,109

[45] Date of Patent: May 30, 1989

[54] SINGLE POSITION NON-INVASIVE CALIBRATION TECHNIQUE

[75] Inventor: Herman Watson, Miami, Fla.

[73] Assignee: Respitrace Corporation, Miami Beach, Fla.

[21] Appl. No.: 120,179

[22] Filed: Oct. 9, 1987

Related U.S. Application Data

[63] Continuation of Ser. No. 24,843, Mar. 18, 1987, abandoned, which is a continuation of Ser. No. 820,604, Jan. 2, 1986, abandoned.

[51] Int. Cl.$^4$ ............................................... A61B 5/08
[52] U.S. Cl. ..................................... 128/721; 128/725
[58] Field of Search ......................... 128/721, 725, 716

[56] References Cited

U.S. PATENT DOCUMENTS

| | | |
|---|---|---|
| 4,267,845 | 5/1981 | Robertson et al. ................. 128/721 |
| 4,308,872 | 5/1982 | Watson et al. ..................... 128/721 |
| 4,373,534 | 2/1983 | Watson ............................... 128/721 |

Primary Examiner—Francis Jaworski
Assistant Examiner—John C. Hanley
Attorney, Agent, or Firm—Schechter, Brucker & Pavane

[57] ABSTRACT

An improved method for calibating a non-invasive apparatus for measuring respiration volume of the type wherein signals indicative of the rib cage and abdomen contributions to respiration volume are provided, and wherein at least one of the signals is multiplied by a predetermined weighting factor for reflecting the relative contributions of the rib cage and abdomen to respiration volume.

The calibration method non-invasively determines the weighting factor by: totaling, during a period of breathing, a plurality of values of a parameter indicative of the relative amplitude, for each breath, of uncalibrated rib cage and abdomen signals; and dividing the average variability of the means of the total of the values of one of the rib cage and abdomen signals by the average variability of the mean of the tota of the values of the other signal. The quotient so derived represents the weighting factor.

An apparatus for calibrating in accordance with the method is also disclosed.

10 Claims, 3 Drawing Sheets

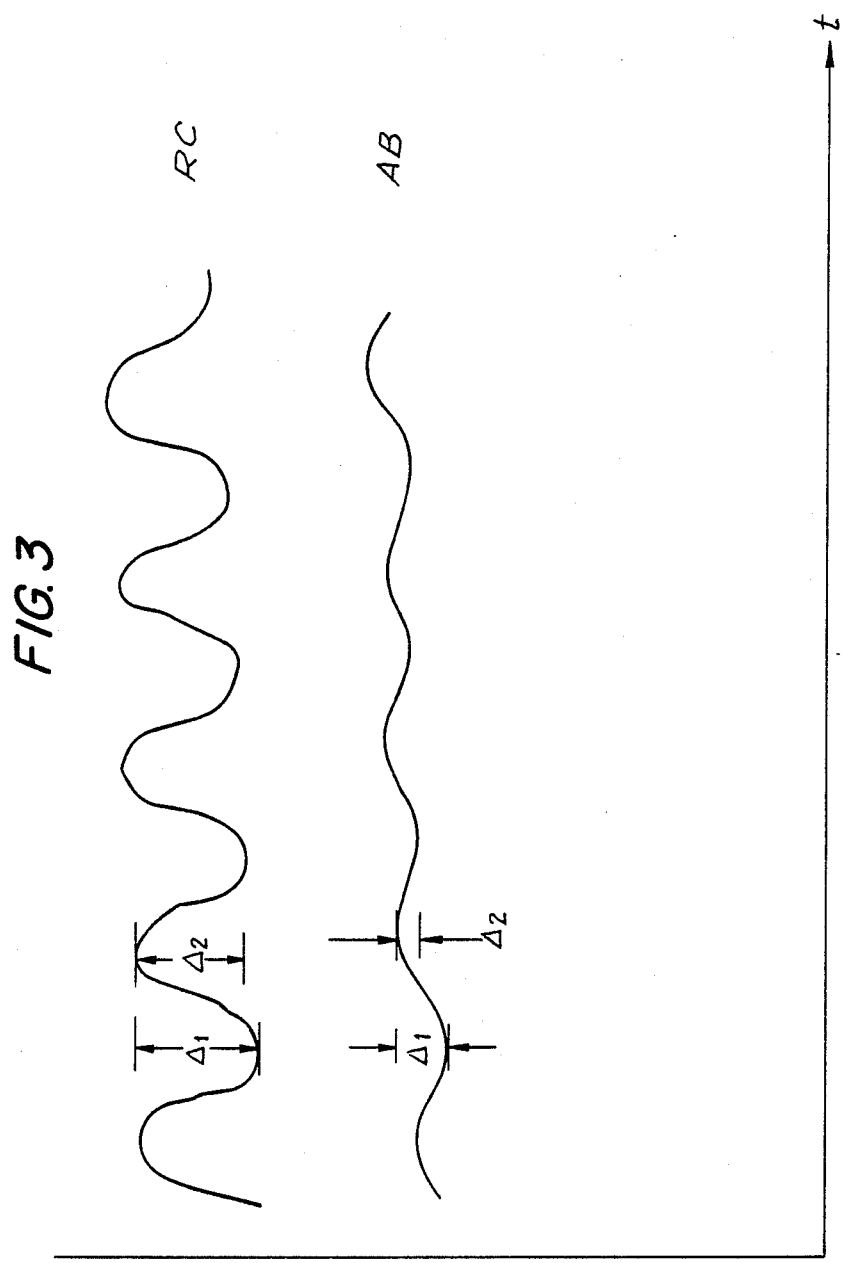

SINGLE POSITION NON-INVASIVE CALIBRATION TECHNIQUE

This is a continuation of U.S. application Ser. No. 024,843, filed Mar. 18, 1987 now abandoned, which is a continuation of U.S. application Ser. No. 820,604, filed Jan. 21, 1986 now abandoned.

TECHNICAL FIELD

This invention pertains to methods and apparatus for measuring respiration volume and, more particularly, to such methods and apparatus which measure respiration volume by separately measuring and then summing the contributions from a plurality of torso portions, such as the rib cage and abdomen. Most particularly, this invention pertains to a calibration technique for weighting signals indicative of the contributions from the torso portions whereby the sum of the signals is proportional to respiration volume.

BACKGROUND ART

U.S. Pat. No. 4,308,872 of Jan. 5, 1982, entitled Method And Apparatus For Monitoring Respiration, the contents of which are incorporated herein by reference in their entirety, discloses a method and apparatus for quantitatively measuring respiration volume. The method disclosed in that patent comprises looping first and second extensible conductors about the rib cage and abdomen, separately and simultaneously measuring the inductances of the conductors during respiration, weighting the measured inductances to reflect the different contributions of the rib cage and abdomen to respiration volume, and summing the weighted measured inductances to obtain actual respiration volume.

As noted, practice of the technique disclosed in the patent requires weighting or calibrating the inductances measured by the abdomen and rib cage conductors. To effect calibration it is necessary to determine the weighting factors K and L to satisfy the following equation:

$$V = K \cdot RC + L \cdot AB \quad \text{[EQUATION A]}$$

where V is total respiration volume, RC is the rib cage contribution to respiration volume as measured at the rib cage conductor and AB is the abdominal contribution as measured at the abdominal conductor. U.S. Pat. No. 4,308,872 discloses a specific technique for determining the values for the weighting factors K and L.

In accordance with that disclosure, a spirometer is employed during the calibration procedure. With the patient in a first position, such as standing, a simultaneous set of readings are recorded from the outputs of the spirometer, the rib cage conductor, and the abdominal conductor. This is repeated with the patient in a second position such as supine. At this point, there are two sets of values for V, RC, and AB which satisfy Equation A. Thus, two equations having two unknowns, the constants K and L, may be written. From these, the weighting factors K and L may be determined by employing well known techniques for solving simultaneous equations. Thus:

$$K = \frac{AB_1 \cdot V_2 - AB_2 \cdot V_1}{RC_2 \cdot AB_1 - RC_1 \cdot AB_2} \quad \text{[EQUATION B]}$$

$$L = \frac{RC_1 \cdot V_2 - V_1 \cdot RC_2}{AB_2 \cdot RC_1 - AB_1 \cdot RC_2} \quad \text{[EQUATION C]}$$

The denominators of Equations B and C may, depending upon the recorded values, approach or equal zero. Clearly, when this happens, the values obtained for K and L will be inaccurate, thereby skewing any measurement based on such weighting factors. Thus, each time the denominators of Equations B and C approach or equal zero, a new set of readings must be taken, thereby increasing the time required for calibration.

In U.S. Pat. No. 4,373,534 of Feb. 15, 1983, entitled Method And Apparatus For Calibrating Respiration Monitoring System, the contents of which are also incorporated herein by reference in their entirety, an alternate method and apparatus for a graphing-based technique for determining the weighting factors K and L is disclosed. As in the simultaneous equation technique of U.S. Pat. No. 4,308,872, a spirometer or other device for independently measuring respiration volume is employed during the calibration procedure. With the subject in a first position, readings from the spirometer, the rib cage conductor and the abdominal conductor are simultaneously recorded for a plurality of breaths, preferably at least three in number. This is repeated with the subject in a second position. For each breath, the rib cage and abdominal readings are divided by the spirometer reading. That is, the values RC/V and AB/V are obtained for each breath, where V is the respiration volume as measured by the spirometer, RC is the rib cage reading from the uncalibrated rib cage conductor, and AB is the abdominal reading from the uncalibrated abdominal conductor. The points (RC/V, AB/V) for each breath are next plotted on a graph whose axes are RC/V and AB/V, and a line approximation is drawn through these points. The line may be drawn by visual approximation, although preferably it is determined by the least squares technique. The line is then extended through the x and y axes. The reciprocals of the x and y intercepts define the weighting factors K and L; i.e. the reciprocal of the intercept of the RC/V axis defines the weighting factor K for the rib cage and the reciprocal of the intercept of the AB/V axis defines the weighting factor L for the abdomen. Preferably, all of the foregoing calculations are carried out by a microprocessor or other data processor which performs the calculations and yields values for the weighting factors K and L.

A drawback of the methods and apparatus disclosed in U.S. Pat. Nos. 4,308,872 and 4,373,534 is the requirement that sets of data points or values—from the abdominal and rib cage conductors and from the spirometer or other respiration volume measurement device—be obtained with the subject for two different distributions of ventilation—i.e. in two separate positions. Where a subject's physiological condition prevents or dictates against movement from one position to another, however, calibration of the rib cage and abdominal conductor contributions cannot be readily carried out in accordance with the known methods.

Another drawback of these prior art methods and apparatus is that in certain applications, such as neonatal monitoring, it is not practical to calibrate the apparatus using an independent respiration volume measuring device such as a spirometer. For example, since the above calibration techniques require airway connection to a spirometer or other similar device, significant time is required to carry out the procedure. This is often unacceptable to new-born nursery staff where time is at a premium.

Yet another problem with these calibration techniques and apparatus is that they rely on the assumption that all air movement in the respiratory system is between the rib cage and spirometer or the abdomen and the spirometer. In fact, there also exists movement of air between the rib cage and the abdomen during normal respiration. This RC-AB exchange of air is pendelluft that occurs continuously and with varying degree in respiration. The known methods do not incorporate an allowance for pendelluft. Another known quantitative calibration technique is described in Single Position Tidal Breathing Calibration of the Respiratory Inductive Plethysmograph, Watson et al, Amer. Rev of Respiratory Diseases, Vol. 129, p. A256 (1984). According to that technique, with the subject in a single position or posture, readings from a spirometer (SP), the rib cage conductor (RC), and the abdominal conductor (AB) are simultaneously recorded for a predetermined period of preferably at least one full breath. The curves (SP, RC) and (SP, AB) are then plotted from the recorded data and each resulting curve is closed by a straight line connnecting its beginning and end point. The resulting loop areas are then calculated as by integration. Then, using any selected data points simultaneously recorded from the spirometer (SP) and from the rib cage (RC) and abdominal (AB) conductors, weighting factors (for the rib cage scaling amplifier and/or for the abdomen scaling amplifier) may be determined. This calibration technique also suffers from the drawback that it is invasive in the sense that it requires a spirometer or other device measuring respiration volume at the mouth.

BRIEF DESCRIPTION OF THE DRAWINGS

In the drawings, wherein like reference numberals denote similar elements throughout the several views:

FIG. 3 is a graphic representation illustrating the delta values for the rib cage and abdominal signals.

SUMMARY OF THE INVENTION

The present invention is an improved method for calibrating a non-invasive apparatus for measuring respiration volume of the type including means for providing a signal responsive to a rib cage dimension indicative of rib cage contribution to respiration volume, means for providing a signal responsive to an abdominal dimension indicative of abdominal contribution to respiration volume, and means for multiplying at least one of the rib cage and abdominal signals by a predetermined weighting factor for reflecting the relative contributions of the rib cage and abdomen to respiration volume.

The improved calibration method for determining the weighting factor comprises totaling, over a baseline period of substantially steady state breathing, a plurality of values of a parameter indicative of the relative amplitude, for each breath, of the uncalibrated rib cage and abdomen signals; dividing the average variability of the mean of the total of the values of one of the rib cage and abdomen signals by the average variability of the mean of the total of the values of the other signal; and then multiplying the other signal by the quotient derived from the dividing step, the quotient representing the weighting factor. An apparatus for calibrating in accordance with the present invention is also disclosed.

Further features and advantages of the present invention will be more fully apparent from the following detailed description and annexed drawings of the presently preferred embodiment thereof.

BEST MODE FOR CARRYING OUT THE INVENTION

Figure 1:
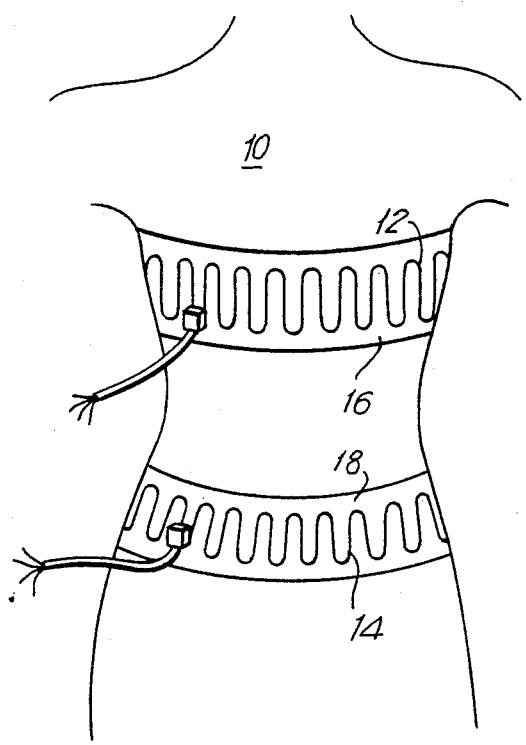
FIG. 1 is a diagrammatic representation of a portion of a system for non-invasively monitoring respiration volume.
Figure 2:
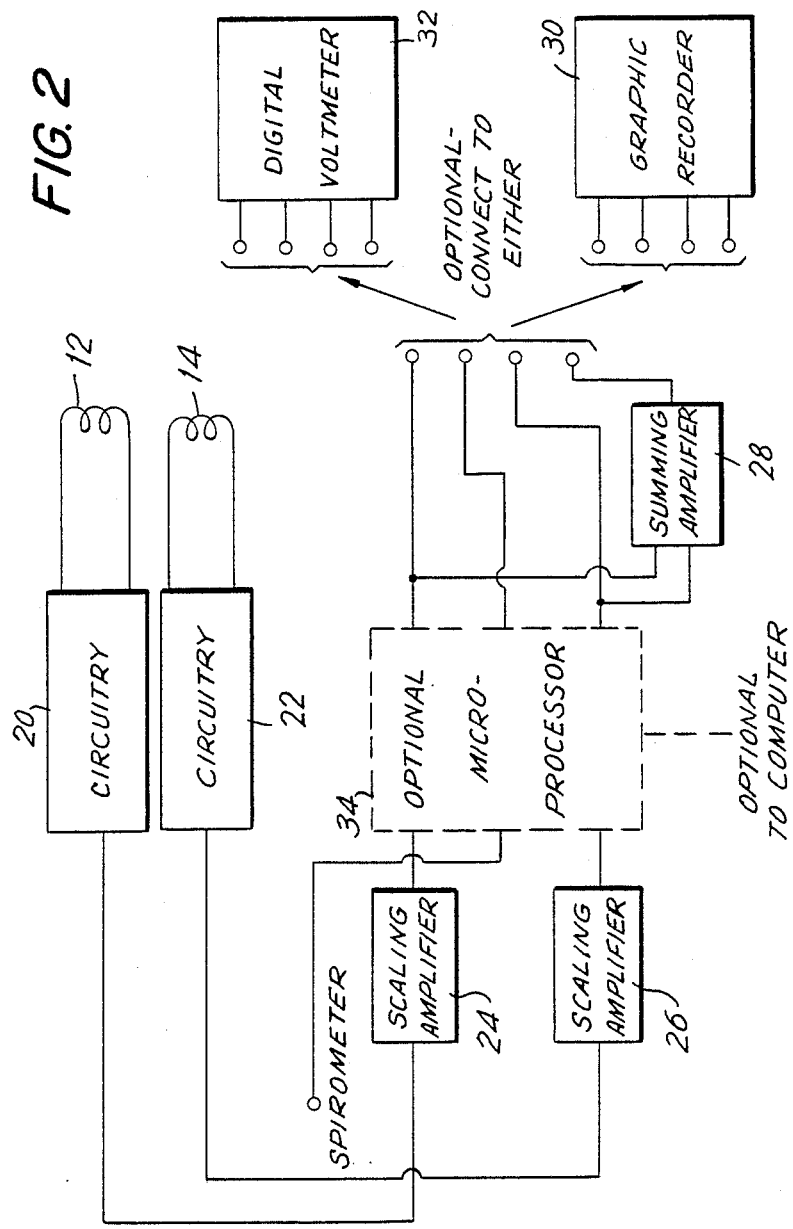
FIG. 2 is a block diagram of a complete system for non-invasively monitoring respiration.

Referring now to the drawings, apparatus for measuring respiration volume of the type disclosed in U.S. Pat. No. 4,306,872 is shown in FIGS. 1 and 2. Two extensible conductive loops 12, 14 are secured in any suitable fashion to elastic tubes 16, 18, respectively, such that the conductors 12 and 14 extend respectively about the rib cage and abdomen of the subject 10. As the subject 10 breathes, the elastic tubes 16, 18 and conductive loops 12, 14 expand and contract, resulting in changes in the inductances of the loops. After the inductance of each loop is converted to a proportional signal, the signals are calibrated and then summed to provide a signal indicative of tidal volume. Calibration of the signals from the rib cage and abdomen conductors 12 and 14, respectively, is necessary because the relative contributions of the rib cage and abdomen to tidal volume vary from subject to subject and even in a single subject with different postures, e.g. standing, supine, etc.

Suitable apparatus for converting the inductances of the conductors 12 and 14 to proportional electrical signals, calibrating those signals to reflect the proper relative contributions, and then summing those signals to provide a signal indicative of tidal volume are known to those of ordinary skill in the art. One such apparatus is disclosed in U.S. Pat. No. 4,306,872. Another suitable apparatus is marketed by Nims, Inc., Miami Beach, Fla. under the model designation Respigraph TM. Such apparatus are generically illustrated in block diagram form in FIG. 2, where the blocks 20, 22 represent, respectively, appropriate circuitry for converting the inductances of the rib cage and abdominal conductors 12, 14 to proportional electrical signals suitable for further processing. The scaling amplifiers 24, 26 represent circuitry for calibrating the signals from the rib cage and abdomen, respectively, to reflect the relative contributions of the rib cage and abdomen to tidal volume. Once the scaling amplifiers 24, 26 are properly calibrated, the resulting signals may be summed, as by the summing amplifier 28 in FIG. 2, to yield a signal indicative of tidal volume. The output signal from the summing amplifier 28 as well as the output signals from the two scaling amplifiers 24 and 26 may then be displayed as on a graphic recorder 30 or a digital voltmeter 32. Optionally, a microprocessor 34 may be incorporated in the apparatus for summing the signals from the scaling amplifiers 24, 26 and/or further processing those signals for diagnostic purposes, all in accordance with techniques known to those of ordinary skill in the art. If the microprocessor 34 is used to sum the signals from the scaling amplifiers, the summing amplifier 28 may be eliminated.

The present invention is for an improved method for calibrating the signals from the rib cage and abdomen such that their sum produces a signal indicative of tidal volume. As is noted above, while various calibration techniques are known to those of ordinary skill in the art, all the known techniques possess drawbacks. Turning to the calibration technique of the invention, from Equation A it is known that:

$$V = (K \times RC) + (L \times AB)$$

where V is total respiration volume or tidal volume, RC is the rib cage contribution to respiration volume as measured by the rib cage conductor and AB is the abdominal contribution to respiration volume as measured by the abdominal conductor. K and L are calibration factors for the rib cage and abdomen, respectively. Another way of expressing this relationship is:

$$V = M \times [(Z \times RC) + AB] \qquad \text{[EQUATION D]}$$

where MxZ is equal to K and M is equal to L. It will be apparent that Equation D separates the calibration components into a proportionality factor Z and a scaling factor M. Using this approach, calibration may be viewed as a two step process. The first step is the determination of the correct proportionality factor Z satisfying Equation D, such that $$V \sim (Z \times RC) + AB \qquad \text{[EQUATION E]}$$

In other words, the proportionality factor Z defines the correct relative contributions of the rib cage (RC) and abdomen (AB) to tidal volume (V). Classically, determination of the proportionality factor Z is determined by an isovolume calibration technique in which the subject breathes against a closed airway i.e. with no volume movement at the mouth, whereby V=0. In other words, during an isovolume maneuver, the only movement of volume is between the rib cage and abdomen compartments, i.e. Penedeluft, since no air escapes through the mouth. Under these conditions, Equation D becomes:

$$0 = (Z \times RC) + AB \qquad \text{[EQUATION F]}$$

or $$Z = -AB/RC \qquad \text{[EQUATION G]}$$

So, by recording the readings from the rib cage and abdomen conductors during the isovolume manuver, the proportionality factor Z can be determined from Equation G. Once Z is determined, the quantity (ZxRC)+AB can be calculated for any point in time from the recorded values of the rib cage and abdomen conductors. Since we know from Equation E that (ZxRC)+AB is always proportional to tidal volume V, a determination of that quantity provides a valuable diagnostic tool. For example, as those of ordinary skill in the art will appreciate, from this quantity obstructive and central apneas can be diagnosed, RC as a percent of tidal volume V can be calculated, and increases and decreases in relative tidal volume V can be assessed.

The difficulty with this approach is that an isovolume maneuver requires breathing against a closed airway, which is not always practical, as in neo-natal and critical care applications. If, on the other hand, the proportionality factor Z and hence the quantity (ZxRC)+AB is to be determined without an isovolume maneuver, it would appear from Equation E that a measurement of tidal volume must be taken, otherwise there will be a single equation with two unknowns, namely, proportionality factor Z and tidal volume V.

In accordance with the present invention, this problem is solved as follows. The rib cage (RC) and abdomen (AB) signals are recorded for a large number of breaths during an initial baseline period. For example, 250 breaths may be measured during quiet breathing over a 10 minute interval. Actually, breathing during the baseline period need not be quiet, as long as it is steady state. For example, the baseline could be derived from breaths recorded during 10 minutes of exercise. During this baseline period, the uncalibrated signals from the rib cage (RC) and abdomen (AB) conductors are recorded. Referring to FIG. 3, for each of these signals, two values or breath "deltas" are calculated for each breath, ($\Delta_1$) being the difference between the signal at the beginning and end of inspiration, the other ($\Delta_2$) being the difference between the beginning and end of expiration. These delta values are then totaled separately for each signal. Assuming 250 breaths during baseline, and since there are two delta values for each breath, the total for each signal will be computed by adding 500 delta values. While the delta values described above are preferred, it should be appreciated that the delta values are employed to provide a parameter indicative of the relative amplitude for each breath of the uncalibrated rib cage and abdomen signals taken during baseline. Accordingly, as used herein, the term delta values means any parameter of the uncalibrated rib cage and abdomen signals which provides this information.

If actual tidal volume were also recorded during baseline, as by spirometry, and the deltas for tidal volume totaled and the mean determined, the following relationship would apply:

$$\text{Mean } SP = \text{Mean } RC + \text{Mean } AB \qquad \text{[EQUATION H]}$$

Where SP is actual tidal volume as determined, e.g. by spirometry. Since the mean values in Equation H are derived from uncalibrated signals, calibration factors are required if the lefthand side in Equation H is to equal the righthand side.

The standard deviations (SD) of the mean values for the tidal volume (SP) rib cage (RC) and abdomen (AB) signals can be calculated. Herein, these will be expressed, respectively, as SD (SP), SD (RC), and SD (AB). If tidal volume (SP) is constant for all breaths recorded during baseline, Equation H can still be computed and the standard deviation of tidal volume, SC (V), is 0.

This situation is analogous to Equation F which, as explained above, applies to the isovolume manuver where V=0. In particular, by considering the standard deviation of a constant tidal volume SD (V), which is also 0, the pendulluft occurring during normal breathing creates a situation analogous to the isovolume situation of Equation F, and taking the variance (Var) of both sides, yields:

$$\text{Var}(Z \times RC) = \text{Var}(AB) \qquad \text{[EQUATION J]}$$

Where variance (Var) is equal to $(SD)^2$. Equation J may be expressed as $$Z^2 \times Var(RC) = Var(AB) \qquad \text{[EQUATION K]}$$

By taking the square root of both sides $$Z \times SD(RC) = SD(AB) \qquad \text{[EQUATION L]}$$

Which yields $$Z = SD(AB)/SD(RC) \qquad \text{[EQUATION M]}$$

It should be appreciated that the standard deviations of the means of the rib cage and abdomen signals is indicative of the average variability of those signals. Accordingly, any analysis that provides an indication of average variability of those signals may be used in lieu of computing standard deviations. Put into other words, it will be apparent from Equation M that the proportionality constant Z for solution of Equation E can be calculated, assuming constant tidal volume breathing during baseline, from the ratio of the standard deviations of AB and RC in a manner analogous to the isovolume manuver, but without the requirement that the airway be blocked. The baseline constant tidal volume assumption required to practice the calibration technique of the invention without invasively recording actual tidal volumes can be satisfied by removing wild points from the 500 delta values of AB and RC computed during baseline as by eliminating values outside of 1.5 standard deviations of the uncalibrated sum of the RC and AB components. With those delta values excluded, the remaining delta values for RC and AB are separately totaled, the means determined, and the standard deviations for the means calculated. The proportionality factor Z can then be calculated from Equation M.

Once the proportionality factor Z is known, the quantity (ZxRC)+AB will always be proportional to actual tidal volume. See Equation E. This quantity can be continuously monitored on a real time basis from the real time rib cage and abdomen signals generated by the apparatus of FIG. 2. Preferably, this quantity is expressed as a percent of (ZxMean RC)+Mean AB where Mean RC and Mean AB are, respectively, the means of the totals of the uncalibrated RC and AB delta values generated at baseline, but exluding the wild points. This is sufficient for the bulk of diagnostic work, such as detecting obstructive and central apneas, hypoapneas, and variations in tidal volume, the latter being important as a diagnostic tool in a wide variety of disorders.

Referring to FIG. 2, assuming the scaling amplifiers have initially been set to unity again, once the proportionality factor Z is determined, the scaling amplifier 24 for the rib cage is adjusted to Z. From Equation E, we then know that the sum of the signals from the scaling amplifiers at the output of the summing amplifier 28 will be preportional to tidal volume. This completes the calibration procedure.

While for most purposes a quantatitive determination of tidal volume is not necessary, quantitive calibration can be achieved once the proportionality factor Z is known. In particular, referring to Equation D, by taking a single measurement of actual tidal volume V, the scaling factor M can be calculated, since ZxRC and AB are available, respectively, at the output of the rib cage and abdomen scaling amplifiers. In other words, there is then only a single unknown in Equation D, the scaling factor M, which is calculated as:

$$M = V/[(Z \times RC) + AB]. \qquad \text{[EQUATION N]}$$

One simple way to take a measurement of actual tidal volume is to simply have the subject inhale a known quantity of air, as from a syringe. Before the subject inhales, this quantity is input to the apparatus of FIG. 2 at the "spirometer" input. The microprocessor 34 can then perform the calculation of Equation N from the values of Z, RC and AB at the end of inspiration from the syringe.

The scaling factor M may be set in the FIG. 2 apparatus by multiplying the gain of the summing amplifier 28 by scaling factor M, whereupon the output of the summing amplifier will be a semi-quantatitive indication of tidal volume. The term semi-quantatitive is used because it has been determined that tidal volume computed in this fashion is ±10% of actual tidal volume as determined by spirometry.

Desirably, the accuracy of the proportionality factor Z is continuously monitored by repeatedly recalculating the proportionality factor at five minute intervals and printing out the resulting value. After the initial calibration procedure, the recalculated value for the proportionality factor Z during each subsequent five minute interval should be 1.0. In the event of a change in the position of the patient or other condition that varies the proportionality factor Z, that will exhibit itself as a reading of Z above or below 1.0. If the variations are too large, i.e. if Z is less than about 0.7 or greater than about 1.3, the calibration routine can be rerun. Suitable visual or audio alarms can be incorporated in the apparatus of FIG. 2 to indicate such excessive variations.

As noted above, the calibration technique in accordance with the present invention may be utilized in connection with an apparatus for monitoring respiration sold by Nims, Inc., Miami Beach, Fla., under its model designation Respigraph™. The Respigraph incorporates a microprocessor. Preferably, the microprocessor is programmed to carry out the calibration technique in accordance with the present invention. A program listing for a suitable program for carrying out the calibration function appears at the end of this description. The program is in assembly language for a Z80 microprocessor as manufactured by Zylog, Inc.

In practice, the Respigraph™ scaling amplifiers for the rib cage and abdomen signals are initially set at unity gain. A 10 minute baseline is then taken. The program automatically computes the delta values for the rib cage and abdomen signals, discards the wild points, computes the mean values for the rib cage and abdomen from the totals of the remaining delta values, computes the standard deviations for those means, and then computes the proportionality factor Z from Equation M. The scaling amplifier for the rib cage is then adjusted to the proportionality factor Z. The real time output from the Respigaph™ representing the sum of the rib cage and abdomen signals is then proportional to tidal volume as explained more fully above. The program also recomputes the proportionality factor Z during each subsequent 5 minute interval. If the recomputed value differs from 1.0 by more than an acceptable amount, the calibration routine can be rerun. The program also computes the scaling factor M from Equation N if instructed to do so upon inputting an actual tidal volume value as derived, e.g., by spirometry. Of course, taking spirometry readings with a spirometer during baseline defeats an objective of the calibration technique in accordance with the invention, namely, to calibrate non-invasively.

While there has been shown and described herein a preferred embodiment of the present invention and certain suggested modifications thereto, it will be apparent that further changes and modifications may be made without departing from the spirit and scope of the invention. Accordingly, the foregoing description should be construed as illustrative and not in the limiting sense, the scope of the invention being defined by the following claims.

I claim:

1. An apparatus for calibrating a non-invasive apparatus for measuring a subject's respiration volume, said measuring apparatus being of the type including means for providing a signal responsive to a rib cage dimension indicative of rib cage contribution to respiration volume, means for providing a signal responsive to an abdominal dimension indicative of abdominal contribution to respiration volume, and means for multiplying at least one of said rib cage and abdominal signals by a predetermined weighting factor for reflecting the relative contributions of said rib cage and abdomen to respiration volume, said calibrating apparatus comprising:

means for separately totaling the delta values for said rib cage and abdominal signals over a baseline period of substantially steady state breathing;

means for dividing the average variability of the mean of the total of said delta values for one of said rib cage or abdominal signals by the average variability of the mean of the total of said delta values for the other signal; and means for adjusting said multiplying means for multiplying said other signal by the quotient determined by said dividing means.

2. The apparatus of claim 1, further comprising means for determining the average variability of the sum of the rib cage and corresponding abdominal signals during the baseline period, and means for discarding the delta values for the rib cage and corresponding abdominal signals whose sum differs from said average variability of the sum by a predetermined amount.

3. The apparatus of claim 1, further comprising means for summing said one signal and said weighted other signal for providing a sum signal proportional to respiration volume.

4. A method for calibrating an apparatus for non-invasively measuring a subject's respiration volume of the type including means for providing a signal responsive to a rib cage dimension indicative of rib cage contribution to respiration volume, means for providing a signal responsive to an abdominal dimension indicative of abdominal contribution to respiration volume, and means for multiplying at least one of said rib cage and abdominal signals by a predetermined weighting factor for reflecting the relative contributions of said rib cage and abdomen to respiration volume, the method comprising non-invasively determining said weighting factor by (a) totaling the delta values for said rib cage signal over a baseline period of substantially steady state breathing;

(b) totaling the delta values for said abdominal signal over a baseline period of substantially steady state breathing;

(c) dividing the average variability of the mean of the total of said delta values for one of said rib cage or abdominal signals by the average variability of the mean of the total of said delta values for the other of said rib cage or abdominal signals; and (d) multiplying said other signal by a weighting factor equaling the quotient derived from step (c).

5. The method of claim 4, further comprising, before said totaling steps, the steps of determining the average variability of the sum of the rib cage and corresponding abdominal signals during said baseline; and discarding the delta values for the rib cage and corresponding abdominal signals whose sum differs from said average variability of the sum by a predetermined amount.

6. The method of claim 4, further comprising the step of summing said one signal and said weighted other signal to provide a sum signal proportional to respiration volume.

7. The method of claim 6, further comprising the step of providing a signal indicative of actual respiration volume over a finite time interval; dividing said actual respiration volume by said sum signal as derived during said time interval for obtaining a scaling factor; and thereafter multiplying said sum signal by said scaling factor for obtaining a signal quantitatively related to actual respiration volume.

8. The apparatus of claim 6, further comprising means for providing a signal indicative of actual respiration volume over a finite time interval, means for dividing said actual respiration volume signal by said sum signal as derived during said time interval for obtaining a scaling factor, and means for multiplying said sum signal by said scaling factor for obtaining a signal quantitatively related to actual respiration volume.

9. The method of claim 4, further comprising the steps of repeating steps (a)-(c) at predetermined intervals using said weighted other signal; and providing an indication if said quotient differs from 1.0 by a predetermined amount.

10. The apparatus of claim 4, further comprising means for recalculating said quotient at predetermined intervals using said weighted other signal, and means for providing an indication if said quotient differs from 1.0 by a predetermined amount.

* * * * *

UNITED STATES PATENT AND TRADEMARK OFFICE
CERTIFICATE OF CORRECTION

PATENT NO. : 4,834,109

DATED : May 30, 1989

INVENTOR(S) : Herman Watson

It is certified that error appears in the above-identified patent and that said Letters Patent is hereby corrected as shown below:

Title page:
Under "Related U.S. Application Data", change "Jan. 2, 1986" to --Jan. 21, 1986--.

In the Abstract:

Line 1, change "calibating" to --calibrating--.

Line 14, change "means" to --mean--.

Line 16, change "tota" to --total--.

Column 3, line 39, change "numberals" to --numerals--.

Column 5, line 37, change "Penedeluft" to --Pendeluft--.

Column 7, line 59, change "preportional" to --proportional--.

Signed and Sealed this

Fifteenth Day of June, 1993

*Attest:*

MICHAEL K. KIRK

*Attesting Officer*   Acting Commissioner of Patents and Trademarks